United States Patent [19]

Britton et al.

[11] 4,163,104

[45] Jul. 31, 1979

[54] HETEROCYCLIC CONTAINING HYDRAZINECARBOTHIOAMIDES

[75] Inventors: Thomas C. Britton; Donald L. Trepanier, both of Midland, Mich.

[73] Assignee: The Dow Chemical Company, Midland, Mich.

[21] Appl. No.: 951,913

[22] Filed: Oct. 16, 1978

Related U.S. Application Data

[60] Division of Ser. No. 818,683, Jul. 25, 1977, which is a continuation-in-part of Ser. No. 769,125, Feb. 16, 1977, abandoned.

[51] Int. Cl.² ............................................. C07D 295/14
[52] U.S. Cl. .................................. 544/160; 546/231; 260/326.43

[58] Field of Search ....................... 544/160; 546/231; 260/326.43

[56] References Cited

PUBLICATIONS

Sharp et al., "Chem. Abstracts", vol. 75 (1971) No. 63183f.

*Primary Examiner*—Natalie Trousof
*Assistant Examiner*—R. W. Ramsuer
*Attorney, Agent, or Firm*—James W. Ambrosius

[57] ABSTRACT

Novel triazolo- or imidazo-benzotriazepines are prepared from 1,3,4-benzotriazepine-2-thiones which in turn are prepared from a 2-aminobenzophenone.

1 Claim, No Drawings

HETEROCYCLIC CONTAINING HYDRAZINECARBOTHIOAMIDES

CROSS-REFERENCE TO RELATED APPLICATIONS

This application is a division of Ser. No. 818,683 filed 7-25-77 which is a continuation-in-part of Ser. No. 769,125 filed 2-16-77 now abandoned.

FIELD OF THE INVENTION

This invention relates to a process for preparing various benzotriazepine-2-thiones and 6-phenyl-s-triazolo or -4H-imidazo-1,3,4-benzotriazepines and to the intermediates used in their preparation.

BACKGROUND OF THE INVENTION

A number of methods for preparing 1,3,4-benzotriazepine-2-ones have been described in the literature. In general, the compounds are prepared by either of two methods from a 2-aminobenzophenone. In the first method, the 2-aminobenzophenone is treated with semicarbazide to give an aminobenzophenone semicarbazone. This product is cyclized to give the benzotriazepine-2-one. See *Bull. Chem. Soc. Jap.*, 43, 135–138 (1970); Japanese publications 70 11,148 (CA 73:25544a) and 70 11,147 (CA 73:25545b). Alternately, a 2-aminobenzophenone hydrazone is treated with phosgene to give the desired benzotriazepine-2-one. See U.S. Pat. No. 3,176,008; *J. Pharm. Sci.* 63(b), 838–41 (1974) and *J. Med. Chem.* 7(3), 386 (1964).

Despite the reported central nervous system activity of the 1,3,4-benzotriazepine-2-ones, the thio analogues are unknown and no satisfactory method for their preparation has been described in the literature.

The sedative and tranquilization effects of 6-phenyl-s-triazolo(4,3-a) (1,3,4)benzotriazepines in mammals is described in U.S. Pat. Nos. 3,891,666 and 3,880,878. These compounds are prepared using a multi-step synthesis from an appropriately substituted 2-aminobenzophenone. The method used by the prior art to prepare these compounds is inefficient thus giving generally poor yields, and the process subjects the intermediates to a harsh oxidation step. For this reason, compounds which contain easily oxidizable moieties such as hydroxy are not readily prepared by the known method.

SUMMARY OF THE INVENTION

The present invention is directed to a novel process for preparing 1,3,4-benzotriazepine-2-thiones and 6-phenyl-triazolo or imidazo(1,3,4) benzotriazepines. The present invention is also directed to novel intermediates used in the preparation of the above-identified compounds and to novel 6-phenyl-triazolo or imidazo(1,3,4-)benzotriazepines which cannot be readily prepared using procedures known in the prior art.

The benzotriazepine-2-thiones which may be prepared using the method of the present invention are represented by the general formula:

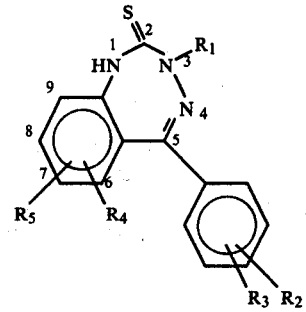

wherein $R_1$ represents a lower alkyl or a substituted lower alkyl wherein the substituent is selected from the group consisting of hydroxy, amino, primary amino, such as, for example, monoloweralkylamino, secondary amino as, for example, diloweralkylamino, or a heterocyclic amine having from 5 to 9 atoms in the ring as, for example, morpholino, piperidino, and pyrollidino; and $R_2$, $R_3$, $R_4$ and $R_5$ independently represent hydrogen, lower alkyl, lower alkoxy, halo or a loweralkylthio.

In addition to serving as intermediates in the preparation of 6-phenyl-triazolo or imidazo(1,3,4)benzotriazepines, compounds falling within the scope have been found to possess central nervous system activity when administered internally to a mammal. They have been found particularly useful in the treatment of central nervous system depression and anxiety.

The 6-phenyl-triazolo or imidazo(1,3,4)benzotriazepines which may be made using the process described herein are represented by the following general formula:

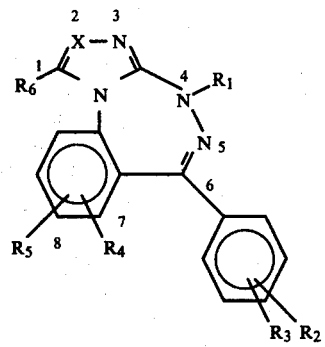

wherein X represents a nitrogen atom or a carbon atom with a hydrogen attached; $R_6$ represents a lower alkyl, a hydroxyloweralkyl, or a cycloalkyl of from 3 to about 7 carbon atoms; and $R_1$, $R_2$, $R_3$, $R_4$ and $R_5$ represent the same moieties as described herein above.

As used in the specification and claims, the term "lower alkyl" refers to an alkyl having from 1 to about 3 carbon atoms. Likewise, terms such as "loweralkylthio", "hydroxyloweralkyl", "loweralkylamino", and the like refer to moieties wherein the alkyl portion is composed of one or more lower alkyls having from 1 to about 3 carbon atoms present. Thus, for example, the term "diloweralkylamino" refers to a moiety of the structure

wherein R represents a lower alkyl as already defined.

Novel compounds within the scope of Formula II above which could not be readily prepared using the process known from the prior art are those compounds wherein X represents a carbon atom with a hydrogen attached and those compounds wherein $R_6$ represents a hydroxyloweralkyl.

The invention also includes the pharmaceutically-acceptable salts of the novel benzotriazpines described herein. As used in the specification and claims, the term "pharmaceutically-acceptable salts" refers to non-toxic acid addition salts of the compounds, the anions of which are relatively innocuous to animals at dosages consistent with good pharmacodynamic activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

The preparation of the 6-phenyl-s-triazolo(4,3-a)(1,3,4)benzotriazepines involve a six-step synthesis. For the purposes of clarity and convenience, the entire process will be divided into two parts. First the preparation of the benzotriazepine-2-thiones will be discussed, and second the preparation of the triazolobenzotriazepines from the benzotriazepine-2-thiones will be explained.

In general, the benzotriazepine-2-thiones are prepared by reacting a 2-aminobenzophenone with thiophosgene to give a novel intermediate, 2-benzoylphenylisothiocyanate. This intermediate is then treated with an alkylhydrazine or substituted alkylhydrazine in a suitable solvent to yield a 2-alkyl (or substituted alkyl)-4-(o-benzoylphenyl)thiosemicarbazide. The thiosemicarbazide intermediate is cyclized to the desired 3-alkyl-2H-1,3,4-benzotriazepine-2-thione by heating the intermediate in a suitable solvent such as, for example, n-propanol or acetic acid or the like. Although the reaction will proceed in the absence of an acid, e.g. acetic acid, the acid does catalyze the reaction. Therefore, various solvent mixtures with acid present may be used to carry out the reaction. The optimal temperature required depends on the solvent or solvent mixture present and the length of time given for the reaction. Optimization of the reaction conditions is dependent on various factors well known to those skilled in the art. The various steps may be summarized as follows:

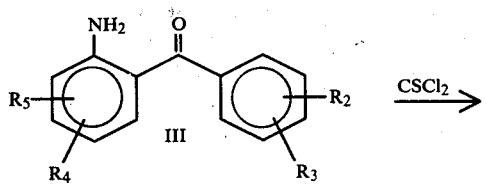

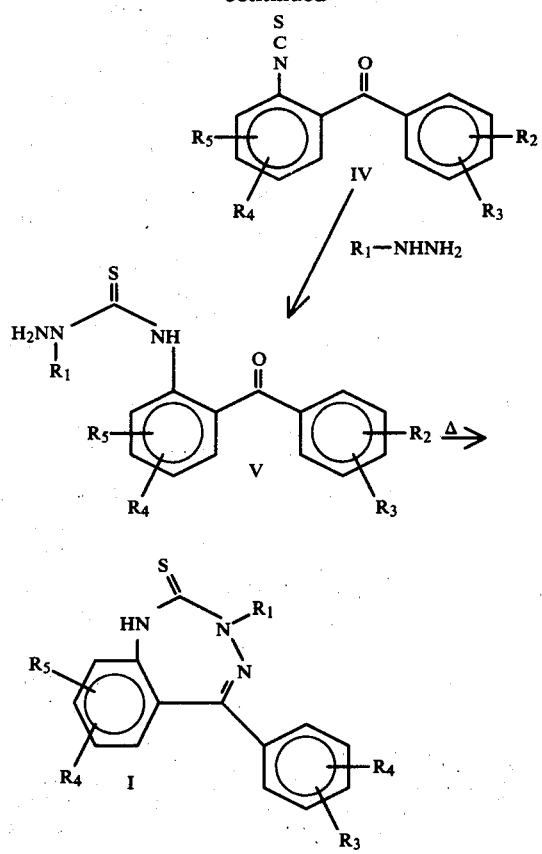

wherein $R_1$, $R_2$, $R_3$, $R_4$ and $R_5$ are the same as defined herein before.

The above method for preparing benzotriazepine-2-thiones has proven to be highly efficient. For example, isolated yields ranging from about 60 to about 90 percent were obtained for the production of the thiosemicarbazide intermediates (V). The benzotriazepines were obtained from the thiosemicarbazide in isolated yields of from about 60 to about 98 percent with the majority of the yields in excess of 90 percent. The 2-benzoylphenylisothiocyanates (IV) are novel intermediates and can also be used in the preparation of 4-hydroxy-3,4-dihydro-2(1H)quinazolinethiones by treatment with a primary amine.

In preparing the triazolobenzotriazepines, the benzotriazepine-2-thione (I) is alkylated by treatment with a strong base in an inert solvent followed by an alkylating agent such as an alkylhalide to give a 2-alkylthio-3H-1,3,4-benzotriazepine. This intermediate is reacted with an excess amount of a pre-selected acylhydrazine, generally under a nitrogen atmosphere, to give the desired 6-phenyl-s-triazolo(4,3a)(1,3,4)benzotriazepine. These reaction steps may be summarized as follows:

 I

-continued

VI + H₂NCH₂CH₂(OR₇)₂ ⟶

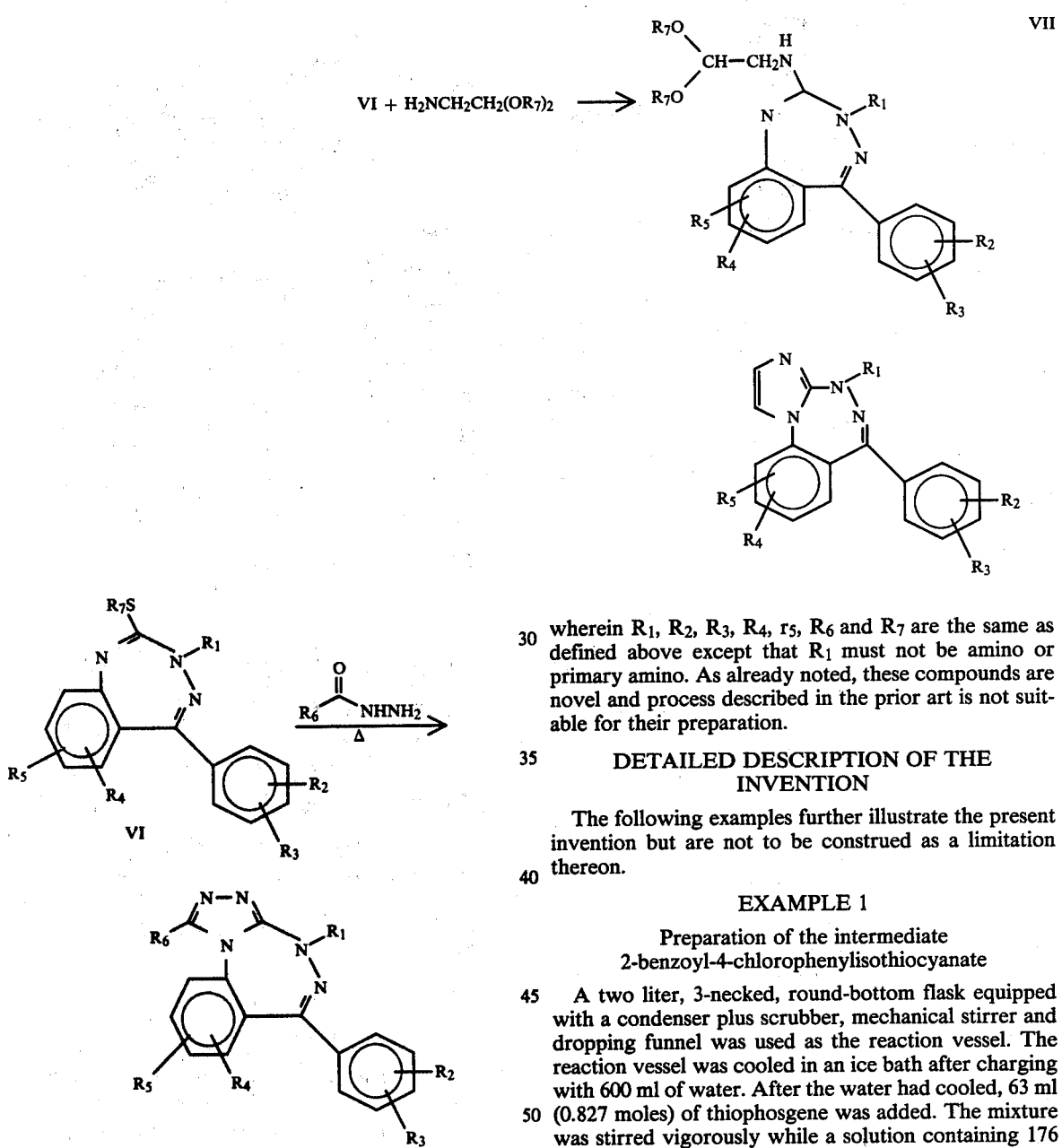

wherein $R_1$, $R_2$, $R_3$, $R_4$, $R_5$ and $R_6$ are as defined above except that $R_1$ must not be amino or primary amino and $R_7$ is an alkyl, generally a lower alkyl, or benzyl the identity of which is immaterial so long as the molecule is not so large as to interfere with the subsequent reactions.

The imidazobenzotriazepines are prepared from the 2-alkylthio-3H-1,3,4-benzotriazepines (VI) already described above. The alkylthiobenzotriazepine (VI) is treated with a pre-selected aminoacetaldehyde dialkyl acetal under heat, generally between about 115° and 150° C. A high boiling solvent such as, for example, 2-ethoxyethanol is usually employed in this reaction. The resulting dialkoxyethylamino-1,3,4-benzotriazepine intermediate is cyclized to the desired 4H-imidazo(1,2-a)(1,3,4)benzotriazepine by heating the intermediate in the presence of a strong acid catalyst. The general reaction sequence may be represented as follows:

wherein $R_1$, $R_2$, $R_3$, $R_4$, $r_5$, $R_6$ and $R_7$ are the same as defined above except that $R_1$ must not be amino or primary amino. As already noted, these compounds are novel and process described in the prior art is not suitable for their preparation.

DETAILED DESCRIPTION OF THE INVENTION

The following examples further illustrate the present invention but are not to be construed as a limitation thereon.

EXAMPLE 1

Preparation of the intermediate 2-benzoyl-4-chlorophenylisothiocyanate

A two liter, 3-necked, round-bottom flask equipped with a condenser plus scrubber, mechanical stirrer and dropping funnel was used as the reaction vessel. The reaction vessel was cooled in an ice bath after charging with 600 ml of water. After the water had cooled, 63 ml (0.827 moles) of thiophosgene was added. The mixture was stirred vigorously while a solution containing 176 grams (0.760 mole) of 2-amino-5-chlorobenzophenone in about 0.5 liter of methylene chloride was added over a period of 20 to 25 minutes. After addition was complete, the funnel was rinsed with about 80 ml of methylene chloride and the reaction mixture was stirred for about one hour with the ice bath in place. Then the ice bath was removed and the reaction mixture was stirred for one additional hour. The organic and aqueous phases were separated, and the aqueous phase was extracted with methylene chloride. The extract was added to the organic phase, and the combined material was dried with magnesium sulfate prior to concentration of the solvent in vacuo. The 2-benzoyl-4-chlorophenylisothiocyanate remained behind as a red oil which solidified on cooling. The product was recrystallized from hexane to leave a cream-colored solid having a melting point of 63-65° C.

Elemental analysis indicated carbon 61.52 percent, hydrogen 2.76 percent, and nitrogen 4.90 percent compared to theoretical values of carbon 61.43 percent, hydrogen 2.95 percent, and nitrogen 5.12 percent.

Other intermediates of formula IV above which exemplify those that can be employed in the practice of the present invention and which were prepared using the general method described above are the following compounds:
2-benzoylphenylisothiocyanate
2-benzoyl-4-bromophenylisothiocyanate
2-benzoyl-4-methylphenylisothiocyanate
(5-chloro-2-isothiocyanatophenyl)(2-chlorophenyl)-methanone marized above. Table I describes other compounds prepared which correspond to the general formula:

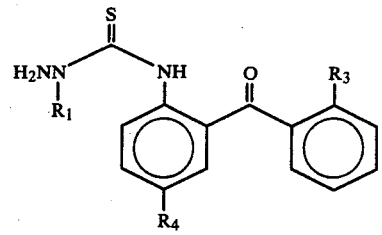

TABLE I

| Intermediate Example No. | $R_1$ | $R_3$ | $R_4$ | M.p. (°C.) | Analysis* C | H | N | S |
|---|---|---|---|---|---|---|---|---|
| 3 | —(CH$_2$)$_2$—OH | H | Cl | 140–2 | 55.05 (54.93) | 4.41 (4.61) | 11.86 (12.01) | 9.30 (9.17) |
| 4 | —(CH$_2$)$_2$—N(CH$_3$)$_2$ | H | Cl | 136.5–138.5 | 57.30 (57.36) | 5.65 (5.62) | 14.86 (14.87) | 8.59 (8.51) |
| 5 | —(CH$_2$)$_3$—N(CH$_3$)$_2$ | H | Cl | 122–4 | 58.55 (58.37) | 5.87 (5.93) | 14.23 (14.33) | 8.33 (8.20) |
| 6 | —(CH$_2$)$_2$—N⌒O | H | Cl | 138.5–141 | 57.1 (57.34) | 5.53 (5.53) | 13.26 (13.37) | 7.48 (7.65) |
| 7 | —(CH$_2$)$_2$—N⌒ | H | Cl | 137–9 | 60.28 (60.49) | 5.99 (6.04) | 13.34 (13.44) | 7.70 (7.69) |
| 8 | —(CH$_2$)$_2$—N(C$_2$H$_5$)$_2$ | H | Cl | 108.5–109.5 | 59.3 (59.32) | 6.24 (6.22) | 13.83 (13.84) | |
| 9 | —(CH$_2$)$_3$—N(C$_2$H$_5$)$_2$ | H | Cl | 115–116 | 60.0 (60.20) | 6.57 (6.50) | 13.53 (13.37) | 7.73 (7.65) |
| 10 | " | H | H | 87–91 | | | | |
| 11 | " | H | Br | 107–9 | 54.0 (54.42) | 6.06 (5.87) | 12.10 (12.09) | |
| 12 | " | H | CH$_3$ | 114–116 | | | | |
| 13 | " | Cl | Cl | | | | | |
| 14 | —(CH$_2$)$_2$—NH$_2$ | H | Cl | 95.5–98 | 54.86 (55.09) | 4.90 (4.91) | 15.97 (16.06) | 9.29 (9.19) |

*Theoretical values are given in parenthesis.

EXAMPLE 2

Preparation of the intermediate N-(2-benzoyl-4-chlorophenyl)-1-methyl-hydrazinecarbothioamide A solution of 5.48 grams (0.02 mole) of 2-benzoyl-4-chlorophenylisothiocyanate in about 50 ml of ethyl ether was added dropwise to a solution containing 1.5 ml (0.028 mole) of methyl hydrazine (98%) in about 50 ml of ethyl ether cooled in an ice bath. Additional ethyl ether was added to facilitate stirring. Following addition of the isothiocyanate, the reaction mixture was stirred at room temperature for about 30 minutes. The solid was collected and washed with additional ethyl ether to yield 5.82 grams (91% yield) of N-(2-benzoyl-4-chlorophenyl)-methyl-hydrazinecarbothioamide as a white solid. The melting point was found to be 168.5°–170° C.

Elemental analysis found carbon 56.21%, hydrogen 4.60%, nitrogen 13.06%, and sulfur 9.98% compared to theoretical values of carbon 56.33%, hydrogen 4.41%, nitrogen 13.14%, and sulfur 10.03%.

In addition to the compound of Example 2 above, other 4-(o-benzoylphenyl)-thiosemicarbazide intermediates were prepared using the general procedure summarized above. Table I describes other compounds prepared which correspond to the general formula:

EXAMPLE 15

Preparation of 7-chloro-1,3-dihydro-3-methyl-5phenyl-2H-1,3,4-benzotriazepine-2-thione A mixture containing 20.0 grams of N-(2-benzoyl-4-chlorophenyl)-methyl-hydrazine-carbothioamide (Example 2) in 250 ml of n-propanol was refluxed for about 2 hours. The mixture was cooled in an ice bath, and the resulting yellow precipitate was collected, washed with isopropanol, and air dried to yield 7-chloro-1,3-dihydro-3-methyl-5-phenyl-2H-1,3,4-benzotriazepine-2-thione as a yellow solid. Additional product was obtained upon evaporation of the solvent under vacuum. The melting point was found to be 188°–190° C.

Elemental analysis of the original precipitate yielded values of carbon 59.60%, hydrogen 3.75%, nitrogen 13.82%, and sulfur 10.65% as compared to theoretical values of carbon 59.69%, hydrogen 4.01%, nitrogen 13.92%, and sulfur 10.63%.

Other 2H-1,3,4-benzotriazepine-2-thiones were prepared using the general procedure explained above. Other compounds corresponding to the formula:

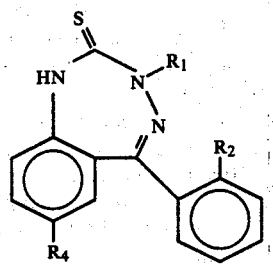

are shown in Table II.

ing with 100 ml of hexane. The resulting yellow product had a melting point of 100° to 102° C. Elemental analysis was used to confirm the structure.

EXAMPLE 28

Using essentially the same procedure as already outlined in Example 27 above, the compound 7-chloro-3-methyl-5-phenyl-2-((phenylmethyl)thio)-3H-1,3,4-benzotriazepine was prepared. The melting point was found to be 125.5°-127.5° C. The structure was confirmed by elemental analysis.

EXAMPLE 29

TABLE II

| Compound Example No. | $R_1$ | $R_2$ | $R_4$ | M.p. (°C.) | Recryst. Solvent | Analysis* C | H | N | S |
|---|---|---|---|---|---|---|---|---|---|
| 16 | $-(CH_2)_2-OH$ | H | Cl | 151-3 | | 57.68 (57.91) | 4.24 (4.25) | 12.46 (12.66) | 9.38 (9.66) |
| 17 | $-(CH_2)_2-N(CH_3)_2$ | H | Cl | 173-5 dec | ethanol | 60.40 (60.24) | 5.47 (5.34) | 15.66 (15.61) | 8.72 (8.93) |
| 18 | $-(CH_2)_3-N(CH_3)_2$ | H | Cl | 117-119 | $CH_2Cl_2$/hexane | 61.35 (61.19) | 5.58 (5.68) | 14.96 (15.02) | 8.77 (8.60) |
| 19 | $-(CH_2)_2-N\diagup\diagdown O$ | H | Cl | 190-2 | isopropanol | 60.00 (59.91) | 5.23 (5.28) | 13.95 (13.98) | 8.00 (8.00) |
| 20 | $-(CH_2)_2-N\diagup\diagdown$ | H | Cl | 131-3 | $CH_2Cl_2$/hexane | 63.14 (63.22) | 5.84 (5.81) | 14.09 (14.04) | 8.20 (8.04) |
| 21 | $-(CH_2)_2-N(C_2H_5)_2$ | H | Cl | 99-101 | hexane | 62.0 (62.08) | 5.94 (5.99) | 14.63 (14.48) | |
| 22 | $-(CH_2)_3-N(C_2H_5)_2$ | H | Cl | 92-4 | hexane | 63.2 (62.9) | 6.25 (6.28) | 13.97 (13.97) | |
| 23 | " | H | H | 108-110 | hexane | 68.8 (68.81) | 7.20 (7.15) | 15.32 (15.29) | |
| 24 | " | H | Br | 107-9 | hexane | 56.3 (56.62) | 5.87 (5.66) | 12.71 (12.58) | |
| 25 | " | H | $CH_3$ | 101-3 | hexane | 69.5 (69.43) | 7.53 (7.42) | 14.79 (14.72) | |
| 26 | " | Cl | Cl | 102-103.5 | | 57.9 (57.93) | 5.46 (5.56) | 12.85 (12.87) | |

*Theoretical values are given in parenthesis.

EXAMPLE 27

Preparation of 7-chloro-3-methyl-2-(methylthio)-5-phenyl-3H-1,3,4-benzotriazepine The reaction vessel was charged with 11.5 grams (479 moles) of sodium hydride (99%) and 850 ml of dry N,N-dimethylformamide. To this mixture, 132 grams (437 moles) of 7-chloro-1,3-dihydro-3-methyl-5-phenyl-2H-1,3,4-bennzotriazepine-2-thione (Example 15) was added with stirring using a screw feed solid addition apparatus while the system was flushed with dry nitrogen. Thirty minutes after addition was complete, the resulting reaction mass was cooled to about 6° C. and 30.0 ml (482 moles) of methyl iodide was added quickly with stirring. The temperature of the reaction mixture rose to about 20° C. The reaction mass was stirred for an additional 30 minutes in an ice bath and for about two hours at ambient temperture. The reaction mixture was poured into about 7 liters of ice water. The yellow precipitate which formed was collected, washed with water, and dissolved in about 1 liter of diethyl ether. The ether solution was washed with water, dried with magnesium sulfate, and concentrated in vacuo on a rotary evaporator. The title compound was left as a viscous yellow-orange oil which solidified on triturat- Preparation of 8-chloro-1,4-dimethyl-6-phenyl-4H-s-triazolo(4,3-a)(1,3,4)benzotriazepine A mixture of 7.25 grams (23.0 m moles) of 7-chloro-3-methyl-(methylthio)-5-phenyl-3H-1,3,4-benzotriazepine (Example 27), 4.8 grams (65 moles) of acethydrazide, and 100 ml of n-butanol was stirred and refluxed under nitrogen for about 17 hours. The solvent was removed in vacuo on a rotary evaporator. The residue was dissolved in methylene chloride. The resulting solution was washed with water, dried with magnesium sulfate, and concentrated in vacuo. The residue was dissolved in a minimum amount of warm carbon tetrachloride. The solution was cooled and seeded with product. The precipitate was collected, washed with cold carbon tetrachloride, and air dried to yield the title compound as a yellow solid. The melting point was found to be 225.5°-227.5° C. The structure was confirmed by elemental analysis.

The title compound was also prepared from 7-chloro-3-methyl-5-phenyl-2-((phenylmethyl)thio)-3H-1,3,4-benzotriazepine (Example 28). The resulting product was confirmed as identical in structure to the product described above.

Other triazolobenzenetriazepine compounds prepared using the general procedure described above include the following:

8-Chloro-4-methyl-6-phenyl-4H-s-triazolo(4,3-a)(1,3,4-benzotriazepine, m.p. 271°–273° C.

8-Chloro-4-methyl-6-phenyl-4H-s-triazolo(4,3-a)(1,3,4)benzotriazepine-1-methanol, m.p. 223°–225° C.

The compound last described is novel and could not be readily prepared using methods generally known to the art. It was found that the compound was active as an anticonvulsant and antidepressant when administered internally to a mammal. The compound was found to be 100% effective as an anticonvulsant when administered at a dose of 60 mg/kg of body weight to mice injected with 85 mg/kg of body weight of Metrazol®. The same dosage was found to be 50% effective against reserpine-induced ptosis in mice.

EXAMPLE 30

Preparation of 8-chloro-4-methyl-6-phenyl-4H-imidazo(1,2-a)(hq3,4)benzotriazepine A mixture of 2.66 grams (8.42 m moles) of 7-chloro-3-methyl-2-(methylthio)-5-phenyl-3H-1,3,4-benzotriazepine, 1.0 grams (9.32 m moles) of aminoacetaldehyde dimethyl acetal (98%), and 10 ml of 2-ethoxyethanol was stirred and refluxed under nitrogen for about 18 hours. The solvent was removed in vacuo on a rotary evaporator, and the residue was dissolved in diethyl ether. The resulting solution was washed in water, dried with magnesium sulfate and concentrated in vacuo. The dark residue was found to be a mixture and was chromatographed on a column containing 170 grams of alumina. The column was washed with benzene. The desired dimethoxyethylamino-1,3,4-benzotriazepine intermediate was obtained on elution with successive portions of methylene chloride and chloroform. The reactions were combined and evaporated to yield a red viscous oil.

The above oil was dissolved in 100 ml of glacial acetic acid. Dry hydrogen chloride gas was bubbled through this solution for about fifteen seconds. The mixture was refluxed for about one and one holf hours after which the solution was concentreated in vacuo on a rotary evaporator and the residue dissolved in chloroform. The chloroform solution was washed with 10% aqueous sodium hydroxide, dried with magnesium sulfate, and concentrated in vacuo to yield a viscous brown oil with solidified on triturating with hexane. The solid was collected and washed with cold hexane to yield the title compound. The final product was recrystallized from hexane and found to have a melting point of 176°–178° C.

Elemental analysis was used to confirm the identity of the product.

As noted above, this compound is novel and could not be readily prepared using methods known to the art. It was found that the compound was active as an anti-inflammatory and antidepressant when administered internally to a mammal. The compound was 100% effective as an anti-inflammatory when administered at a dose of 15 mg/kg of body weight to mice injected with 0.1% aqueous hydrochloric acid at 0.01 ml/grams body weight. The same dose was found to be 25% effective against reserpine-induced ptosis in mice.

We claim:

1. A compound of the formula

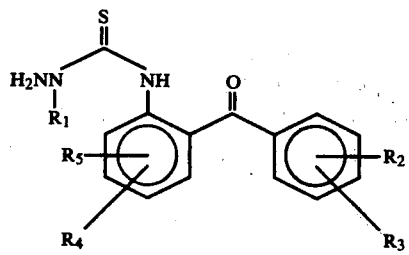

wherein $R_1$ represents a substituted lower alkyl wherein the substituent is selected from the group consisting of morpholino, piperidino or pyrollidino and $R_2$, $R_3$, $R_4$ and $R_5$ independently represent hydrogen, lower alkyl, halo or loweralkylthio.

* * * * *